US00PP26844P2

(12) United States Plant Patent
Peters

(10) Patent No.: US PP26,844 P2
(45) Date of Patent: Jun. 21, 2016

(54) ***MANDEVILLA* PLANT NAMED 'SUNPARAMAKUHO'**

(50) Latin Name: *Mandevilla hybrida*
Varietal Denomination: SUNPARAMAKUHO

(71) Applicant: Marc Peters, Kranenburg (DE)

(72) Inventor: Marc Peters, Kranenburg (DE)

(73) Assignee: Suntory Flowers Limited, Tokyo (JP)

( * ) Notice: Subject to any disclaimer, the term of this patent is extended or adjusted under 35 U.S.C. 154(b) by 58 days.

(21) Appl. No.: 14/121,542

(22) Filed: Sep. 17, 2014

(51) Int. Cl.
*A01H 5/02* (2006.01)

(52) U.S. Cl.
USPC ..... Plt./232

(58) Field of Classification Search
USPC ..... Plt./232
See application file for complete search history.

*Primary Examiner* — Anne Grunberg
(74) *Attorney, Agent, or Firm* — C. A. Whealy

(57) ABSTRACT

A new and distinct cultivar of *Mandevilla* plant named 'Sunparamakuho', characterized by its compact vining plant habit with short internodes; vigorous growth habit; freely branching habit; dark green-colored leaves; freely flowering habit; white-colored flowers; and long flowering period.

1 Drawing Sheet

Botanical designation: *Mandevilla hybrida.*
Cultivar denomination: 'SUNPARAMAKUHO'.

BACKGROUND OF THE INVENTION

The present invention relates to a new and distinct cultivar of *Mandevilla* plant, botanically known as *Mandevilla hybrida* and hereinafter referred to by the name 'Sunparamakuho'.

The new *Mandevilla* plant is a naturally-occurring branch mutation of *Mandevilla hybrida* 'Sunparapibra', disclosed in U.S. Plant Pat. No. 19,649. The new *Mandevilla* plant was discovered and selected by the Inventor on a single flowering plant from within a population of plants of 'Sunparapibra' in a controlled greenhouse environment in Kranenburg, Germany on Jul. 13, 2012.

Asexual reproduction of the new *Mandevilla* plant by cuttings in Kranenburg, Germany since Jul. 24, 2012 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunparamakuho'. These characteristics in combination distinguish 'Sunparamakuho' as a new and distinct *Mandevilla* plant:

1. Compact vining plant habit with short internodes.
2. Vigorous growth habit.
3. Freely branching habit.
4. Dark green-colored leaves.
5. Freely flowering habit.
6. White-colored flowers.
7. Long flowering period.

Plants of the new *Mandevilla* can be compared to plants of the parent, 'Sunparapibra'. Plants of the new *Mandevilla* differ primarily from plants of 'Sunparapibra' in flower color as plants of 'Sunparapibra' have light pink-colored flowers.

Plants of the new *Mandevilla* can be compared to plants of *Mandevilla hybrida* 'Sunparaosiro', disclosed in U.S. Plant Pat. No. 25,134. In side-by-side comparisons conducted in Higashiomi, Shiga, Japan, plants of the new *Mandevilla* differed from plants of 'Sunparaosiro' in the following characteristics:

1. Plants of the new *Mandevilla* had thicker lateral branches than plants of 'Sunparaosiro'.
2. Plants of the new *Mandevilla* had smaller leaves than plants of 'Sunparaosiro'.
3. Plants of the new *Mandevilla* had smaller flowers than plants of 'Sunparaosiro'.
4. Plants of the new *Mandevilla* were more freely flowering than plants of 'Sunparaosiro'.
5. Plants of the new *Mandevilla* and 'Sunparaosiro' differed in flower color as plants of 'Sunparaosiro' had very light pink-colored flowers.
6. Plants of the new *Mandevilla* had shorter peduncles than plants of 'Sunparaosiro'.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph at the top of the sheet comprises a side perspective view of a typical flowering plant of 'Sunparamakuho' grown in a container.

The photograph at the bottom of the sheet is a close-up view of a typical flower of 'Sunparamakuho'.

DETAILED BOTANICAL DESCRIPTION

The aforementioned photographs and following observations, measurements and values describe plants grown during the autumn in 18-cm containers in an outdoor nursery in Higashiomi, Shiga, Japan and under cultural practices typical of commercial *Mandevilla* production. During the production of the plants, day temperatures averaged 25° C. and night temperatures averaged 15° C. Plants were five months old when the photographs and detailed description were taken. In the following description, color references are made to The Royal Horticultural Society Colour Chart, 2007 Edition, except where general terms of ordinary dictionary significance are used.

Botanical classification: *Mandevilla hybrida* 'Sunparamakuho'.

Parentage: Naturally-occurring branch mutation of *Mandevilla hybrida* 'Sunparapibra', disclosed in U.S. Plant Pat. No. 19,649.

Propagation:

*Type*.—By vegetative cuttings.

*Time to initiate roots*.—About two weeks at temperatures about 23° C. to 25° C.

*Time to produce a rooted young plant*.—About five to six weeks at temperatures about 23° C. to 25° C.

*Root description*.—Fibrous; light brown in color.

*Rooting habit*.—Freely branching; medium density.

Plant description:

*Plant and growth habit*.—Compact vining plant habit with relatively short internodes; vigorous growth habit; freely branching habit.

*Lateral branch description*.—Length: About 50 cm. Diameter: About 3.7 mm. Internode length: About 2.6 cm. Strength: Strong, flexible. Texture: Smooth, glabrous. Color: Close to 144A.

Leaf description:

*Arrangement*.—Opposite, simple.

*Length*.—About 5.7 cm.

*Width*.—About 3.6 cm.

*Shape*.—Elliptical.

*Apex*.—Cuspidate.

*Base*.—Obtuse.

*Margin*.—Entire.

*Texture, upper and lower surfaces*.—Smooth, glabrous.

*Venation pattern*.—Pinnate, reticulate.

*Color*.—Developing leaves, upper surface: Close to 146A. Developing leaves, lower surface: Close to 144A. Fully expanded leaves, upper surface: Close to N137A; venation, close to 144B. Fully expanded leaves, lower surface: Close to 138A; venation, close to 144C.

*Petiole length*.—About 1.2 cm.

*Petiole diameter*.—About 1.5 mm.

*Petiole texture, upper and lower surfaces*.—Smooth, glabrous.

*Petiole color, upper and lower surfaces*.—Close to 144A.

Flower description:

*Flower type and habit*.—Single salverform flowers arranged in axillary racemes; flowers face upright to outwardly; freely flowering habit with about six flowers per inflorescence and about 41 inflorescences developing per plant during the flowering season.

*Natural flowering season*.—Plants begin flowering about six weeks after planting; long flowering period, plants flower continuously from summer to late autumn in Japan.

*Flower longevity on the plant*.—About seven to ten days; flowers not persistent.

*Fragrance*.—None detected.

*Inflorescence height*.—About 15.3 cm.

*Inflorescence diameter*.—About 13.1 cm.

*Flowers*.—Appearance: Salverform; flared trumpet, corolla fused and five-parted; flowers roughly star-shaped. Diameter: About 7.75 cm. Depth (length): About 7.1 cm. Throat diameter: About 1.8 cm. Tube length: About 4.8 cm. Tube diameter, mid-section: About 1.2 cm. Tube diameter, base: About 4.1 mm.

*Flower buds*.—Height: About 6.9 cm. Diameter: About 1.4 cm. Shape: Lenticular. Color: Close to 11D and 65C.

*Corolla*.—Quantity and arrangement: Five petals arranged in a single whorl and fused towards the base into an elongated tube. Petal lobe length: About 3.4 cm. Petal lobe width: About 2.9 cm. Petal lobe shape: Roughly orbicular. Petal lobe apex: Cuspidate. Petal lobe margin: Entire; slightly reflexing. Petal lobe texture, upper and lower surfaces: Smooth, glabrous; satiny. Throat texture: Smooth, glabrous; satiny. Tube texture: Smooth, glabrous; satiny. Color: Petal lobe, when opening, upper surface: Close to N155C. Petal lobe, when opening, lower surface: Close to N155B. Petal lobe, fully opened, upper and lower surfaces: Close to NN155B. Throat: Close to 17A. Tube: Close to NN155B.

*Calyx*.—Quantity and arrangement: Five sepals arranged in a single whorl; calyx, star-shaped. Sepal length: About 9 mm. Sepal width: About 2.8 mm. Sepal shape: Narrowly deltoid. Sepal apex: Acuminate. Sepal base: Obtuse. Sepal margin: Entire. Sepal texture, upper and lower surfaces: Smooth, glabrous. Sepal color: When developing, upper surface: Close to 144C; at the apex, close to 47B. When developing, lower surface: Close to 144D; at the apex, close to 47B. Fully opened, upper and lower surfaces: Close to 144D; at the apex, close to 47C.

*Peduncles*.—Length: About 2.6 cm. Diameter: About 1.7 mm. Texture: Smooth, glabrous. Aspect: Upright to outwardly. Color: Close to 143C.

*Pedicels*.—Length: About 1.8 cm. Diameter: About 2.4 mm. Texture: Smooth, glabrous. Aspect: Outwardly to upright. Color: Close to 144C.

*Reproductive organs*.—Stamens: Quantity and arrangement: Typically five; filaments fused to corolla; anthers, connivent. Anther shape: Ellipsoidal. Anther length: About 9.2 mm. Anther color: Close to 10A. Pollen amount: Moderate. Pollen color: Close to 4D. Pistils: Quantity: Typically one. Pistil length: About 2.2 cm. Style color: Close to 154C. Stigma shape: Conical. Stigma color: Close to 150D. Ovary color: Close to 144B.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Garden performance: Plants of the new *Mandevilla* have been observed to tolerate wind, rain and temperatures ranging from about 4° C. to about 30° C.

It is claimed:

1. A new and distinct *Mandevilla* plant named 'Sunparamakuho' as illustrated and described.

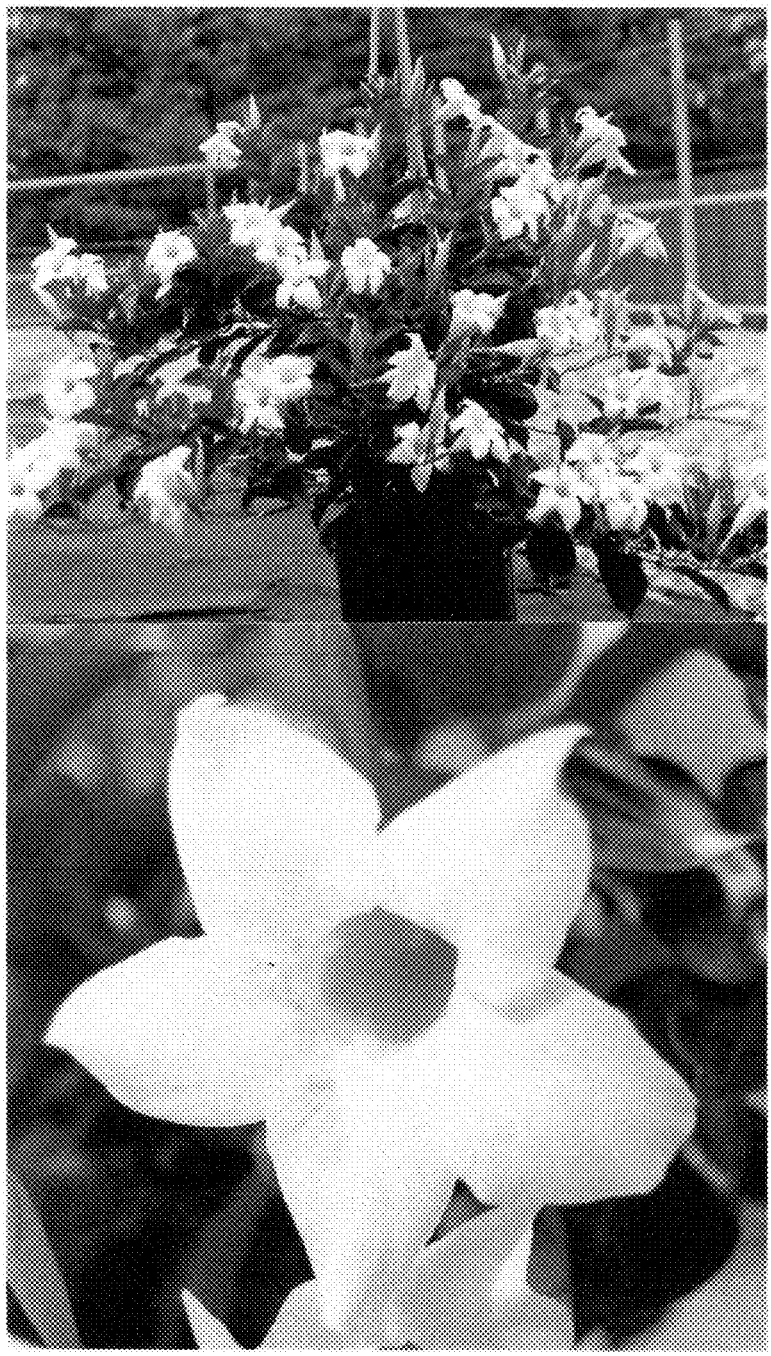

* * * * *